United States Patent
Foley et al.

(10) Patent No.: US 10,449,329 B2
(45) Date of Patent: Oct. 22, 2019

(54) INTERMITTENT URINARY CATHETER ASSEMBLY AND AN ADAPTER ASSEMBLY FOR AN INTERMITTENT URINARY CATHETER

(71) Applicant: Hollister Incorporated, Libertyville, IL (US)

(72) Inventors: Adam J. Foley, Swords (IE); Brendan J. Heneghan, Louisburgh (IE); David Hannon, Ballina (IE); Jerome A. Henry, Castlebar (IE); Michael G. Murray, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 423 days.

(21) Appl. No.: 14/436,154

(22) PCT Filed: Mar. 14, 2013

(86) PCT No.: PCT/US2013/031468
§ 371 (c)(1),
(2) Date: Apr. 16, 2015

(87) PCT Pub. No.: WO2014/062225
PCT Pub. Date: Apr. 24, 2014

(65) Prior Publication Data
US 2015/0273183 A1 Oct. 1, 2015

Related U.S. Application Data

(60) Provisional application No. 61/716,176, filed on Oct. 19, 2012.

(51) Int. Cl.
*A61M 25/00* (2006.01)
*A61M 39/10* (2006.01)

(52) U.S. Cl.
CPC .... *A61M 25/0023* (2013.01); *A61M 25/0017* (2013.01); *A61M 25/0021* (2013.01);
(Continued)

(58) Field of Classification Search
CPC .......... A61M 25/0023; A61M 25/0017; A61M 25/0021; A61M 25/0111; A61M 25/002; A61M 39/10
See application file for complete search history.

(56) References Cited

U.S. PATENT DOCUMENTS 3,742,953 A * 7/1973 Lee .......................... A61F 5/453
128/DIG. 15
3,832,999 A * 9/1974 Crilly .................... A61F 5/4405
604/185

(Continued)

FOREIGN PATENT DOCUMENTS

WO    WO0162182 A2    8/2001
WO    WO2006045809 A1    5/2006

(Continued)

OTHER PUBLICATIONS

Notification of Transmittal of the International Search Report and the Written Opinion of the ISA for PCT/US2013/031468 dated Jul. 25, 2013 (Jul. 25, 2013).

(Continued)

*Primary Examiner* — Ariana Zimbouski
(74) *Attorney, Agent, or Firm* — Cook Alex Ltd.

(57) ABSTRACT

An intermittent urinary catheter assembly (20) comprises a catheter tube (22) having a proximal insertion end (24) and a distal end (26) remote from the proximal insertion end and a lumen (28) which extends from at or near the proximal insertion end to the distal end for draining urine from a human bladder. The intermittent urinary catheter assembly includes a urine discharge sleeve (34) associated with the (Continued)

discharge opening (30) of the catheter tube, and the urine discharge sleeve has a compact stowed configuration and is extendable into a deployed configuration for directing urine flow. Alternatively, an adapter assembly (50") comprises a fitting or nipple (52") having a urine passageway for insertion into a funnel (40") associated with a urine discharge end of an intermittent urinary catheter, and a discharge funnel (42") associated with the fitting or nipple, and an extendable urine discharge sleeve (34") within the discharge funnel.

19 Claims, 6 Drawing Sheets

(52) U.S. Cl.
CPC ..... *A61M 39/10* (2013.01); *A61M 2025/0025* (2013.01); *A61M 2025/0098* (2013.01); *A61M 2039/1077* (2013.01); *A61M 2210/1085* (2013.01); *A61M 2210/1089* (2013.01)

(56) References Cited

U.S. PATENT DOCUMENTS

| | | | |
|---|---|---|---|
| 4,029,099 A * | 6/1977 | Fifield | A61M 39/08 128/912 |
| 5,242,398 A | 9/1993 | Knoll et al. | |
| 5,405,336 A * | 4/1995 | Austin | A61M 25/0014 604/534 |
| 5,454,798 A | 10/1995 | Kubalak et al. | |
| 6,217,569 B1 | 4/2001 | Fiore | |
| 6,668,388 B2 | 12/2003 | Buttigieg | |
| 7,094,220 B2 | 8/2006 | Tanghoj et al. | |
| 7,311,698 B2 | 12/2007 | Tanghoj et al. | |
| 7,380,658 B2 | 6/2008 | Murray et al. | |
| 7,662,146 B2 | 2/2010 | House | |
| 7,682,353 B2 | 3/2010 | Tanghoj et al. | |
| 7,789,873 B2 | 9/2010 | Kubalak et al. | |
| 7,886,907 B2 | 2/2011 | Murray et al. | |
| 7,918,831 B2 | 4/2011 | House | |
| 7,922,712 B2 | 4/2011 | Tanghoj et al. | |
| 2004/0133226 A1 * | 7/2004 | Buckman | A61B 17/3415 606/167 |
| 2005/0049577 A1 | 3/2005 | Snell et al. | |
| 2006/0025753 A1 * | 2/2006 | Kubalak | A61M 25/0017 604/544 |
| 2006/0142736 A1 * | 6/2006 | Hissink | A61F 11/002 604/540 |
| 2007/0225688 A1 | 9/2007 | Goodwin | |
| 2007/0244468 A1 * | 10/2007 | Kostandaras | A61M 39/08 604/523 |
| 2008/0091145 A1 | 4/2008 | House | |
| 2008/0179208 A1 | 7/2008 | Murray et al. | |
| 2008/0228175 A1 | 9/2008 | Snell et al. | |
| 2010/0016821 A1 * | 1/2010 | Bjerregaard | A61F 5/453 604/349 |
| 2010/0130949 A1 * | 5/2010 | Garcia | A61M 1/0019 604/326 |
| 2010/0198195 A1 * | 8/2010 | Nishtala | A61L 29/04 604/544 |
| 2010/0204682 A1 | 8/2010 | Tanghoj et al. | |
| 2010/0211049 A1 | 8/2010 | Schertiger et al. | |
| 2010/0211050 A1 | 8/2010 | Luther | |
| 2010/0263327 A1 | 10/2010 | Murray et al. | |
| 2011/0049866 A1 * | 3/2011 | Trombley, III | A61M 5/007 285/20 |
| 2011/0120892 A1 * | 5/2011 | Frederiksen | A61M 25/002 206/210 |

FOREIGN PATENT DOCUMENTS

| | | |
|---|---|---|
| WO | WO2008103644 A1 | 8/2008 |
| WO | WO2013029622 A1 | 3/2013 |

OTHER PUBLICATIONS

Australian Office Action, dated Jan. 12, 2016, for Australian Patent Application No. 2013332448.

* cited by examiner

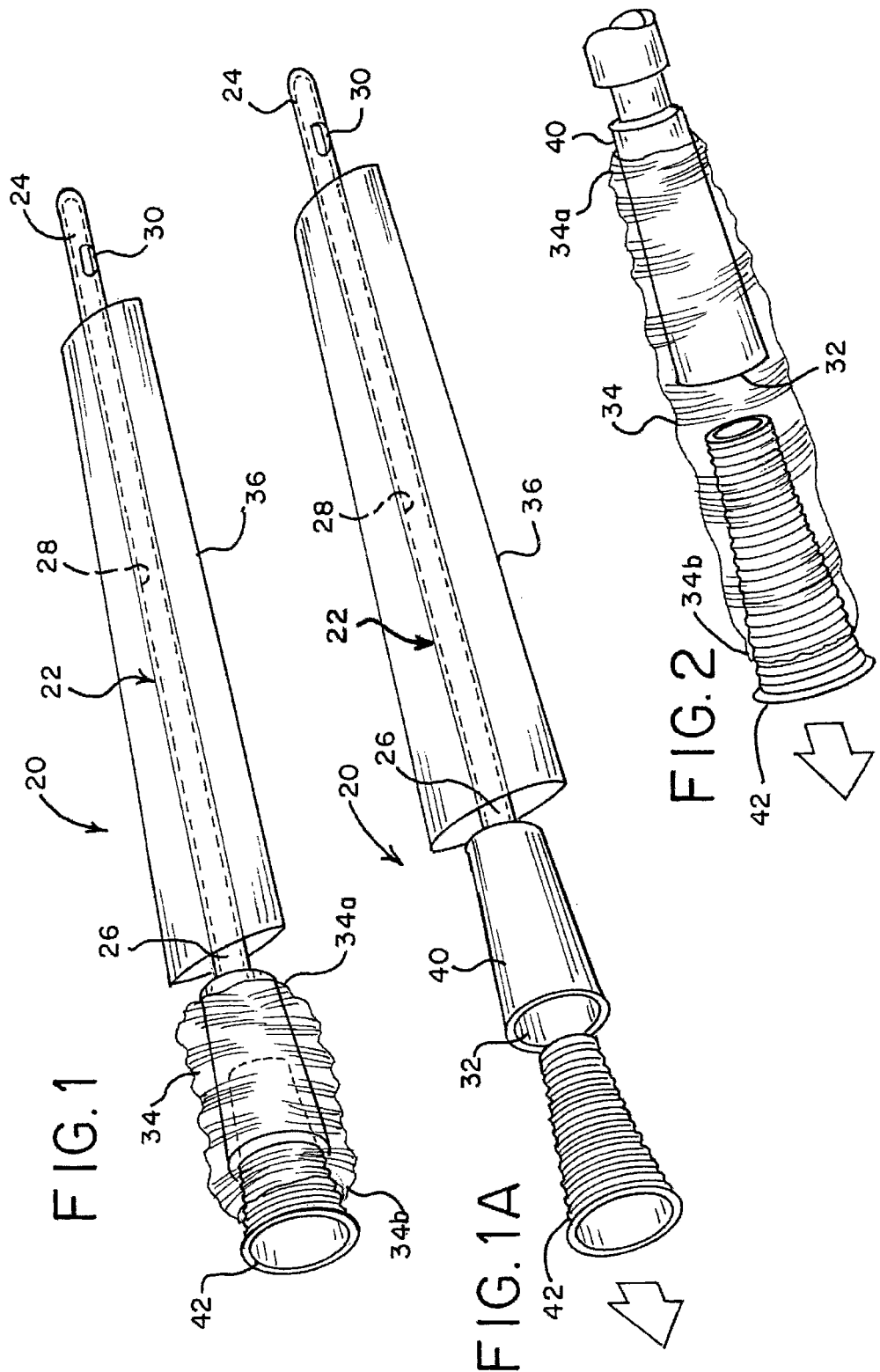

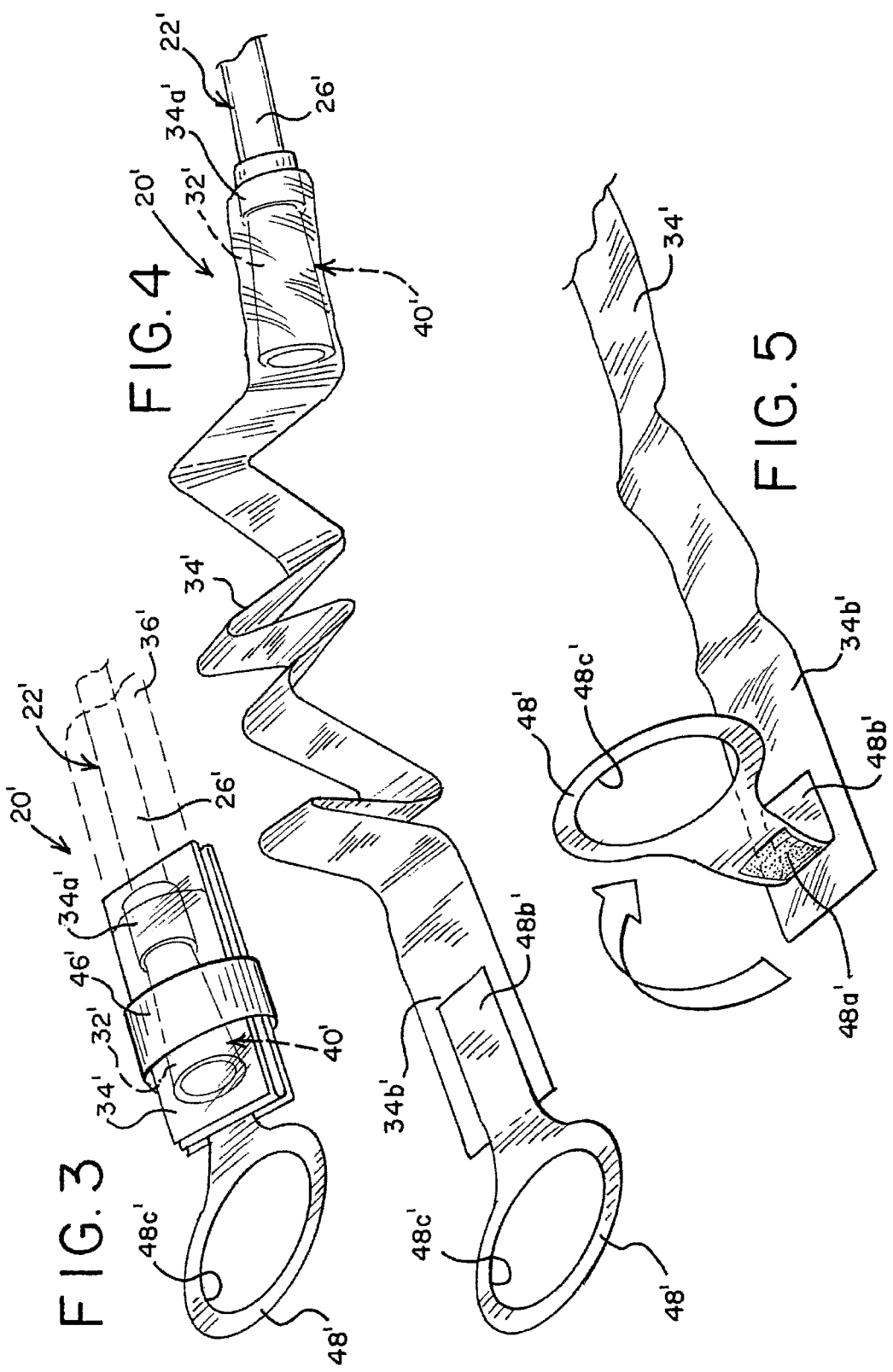

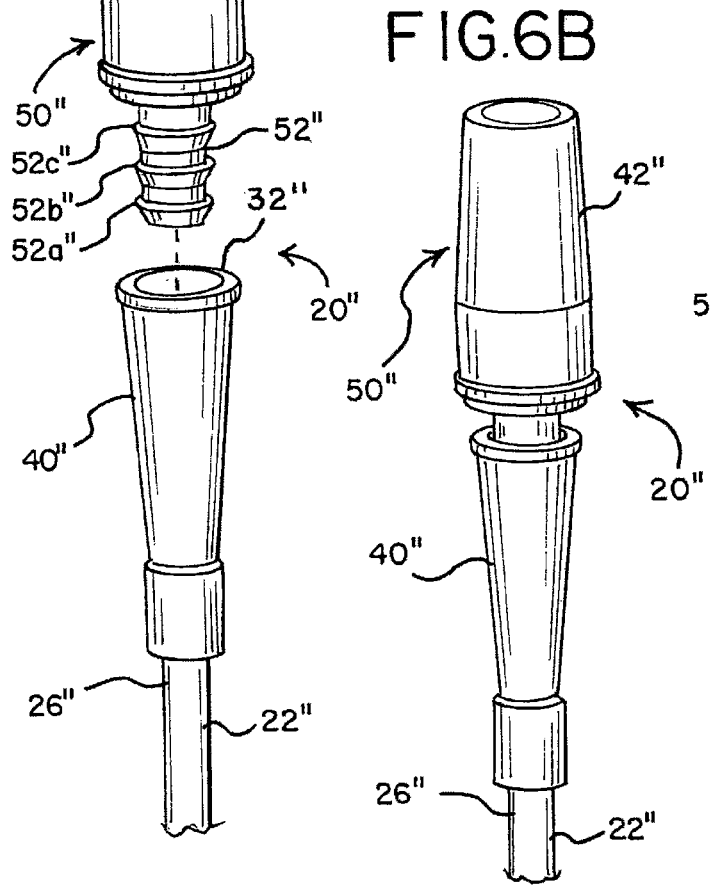

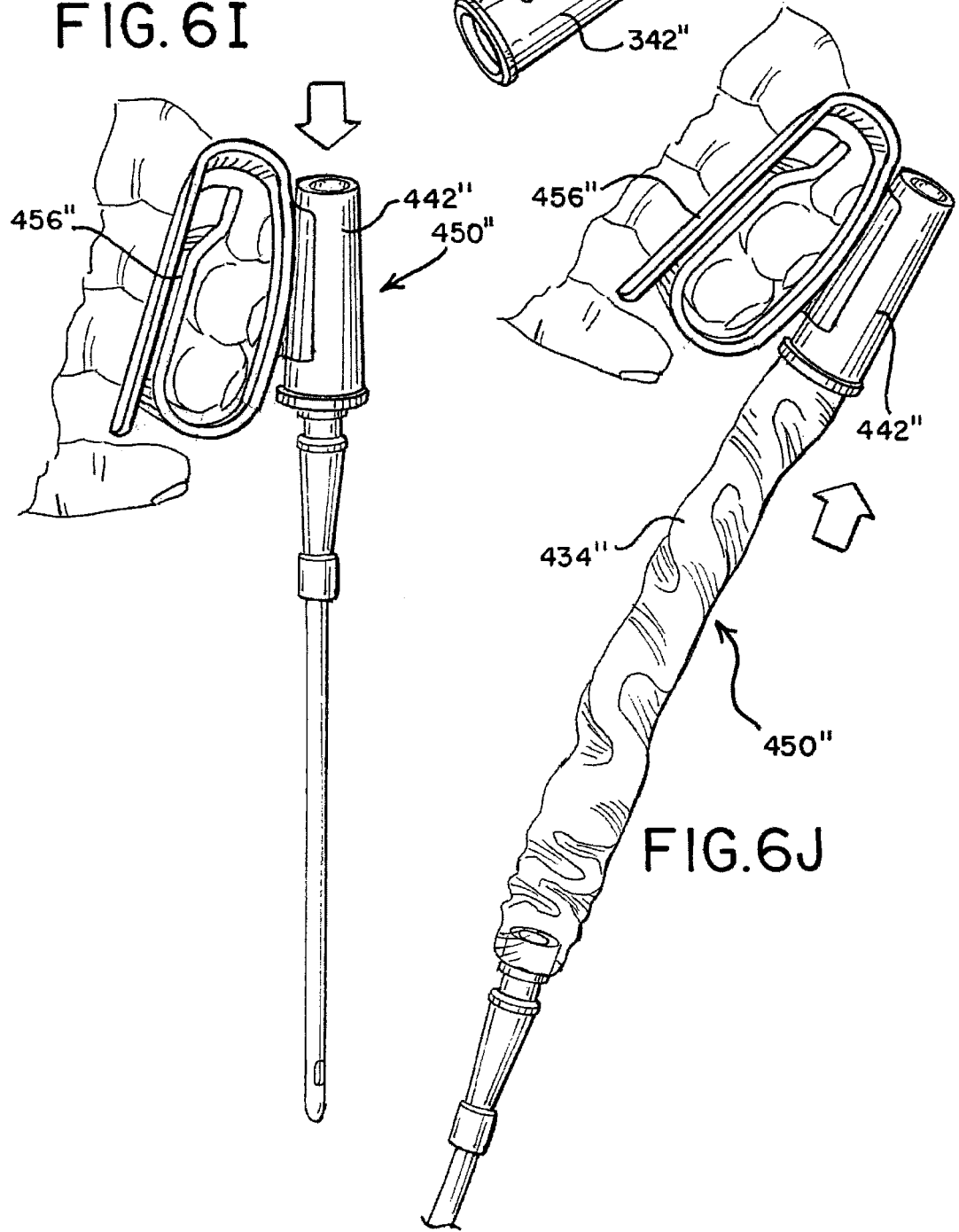

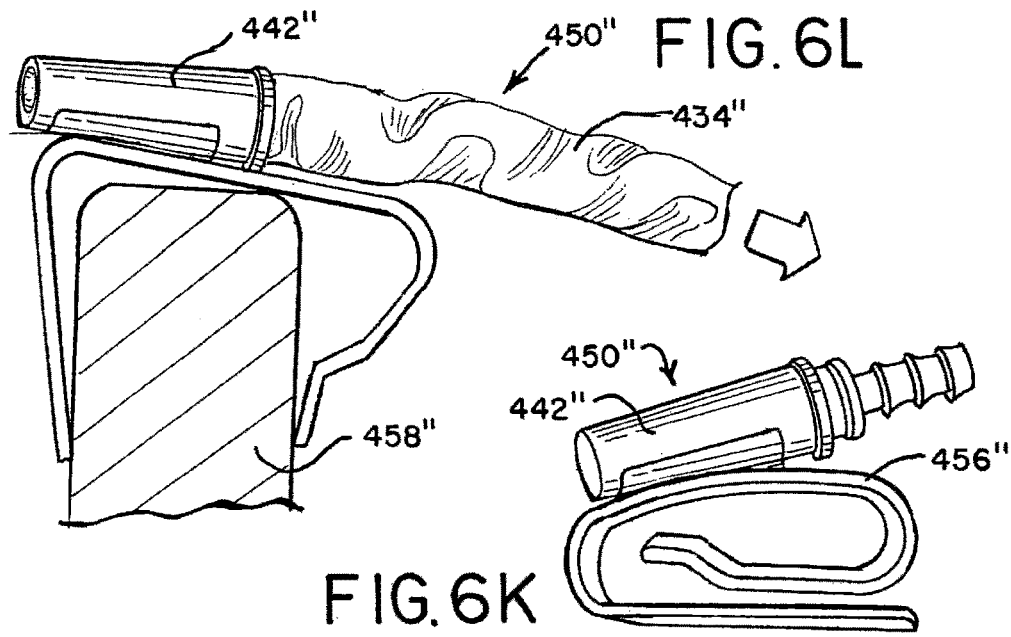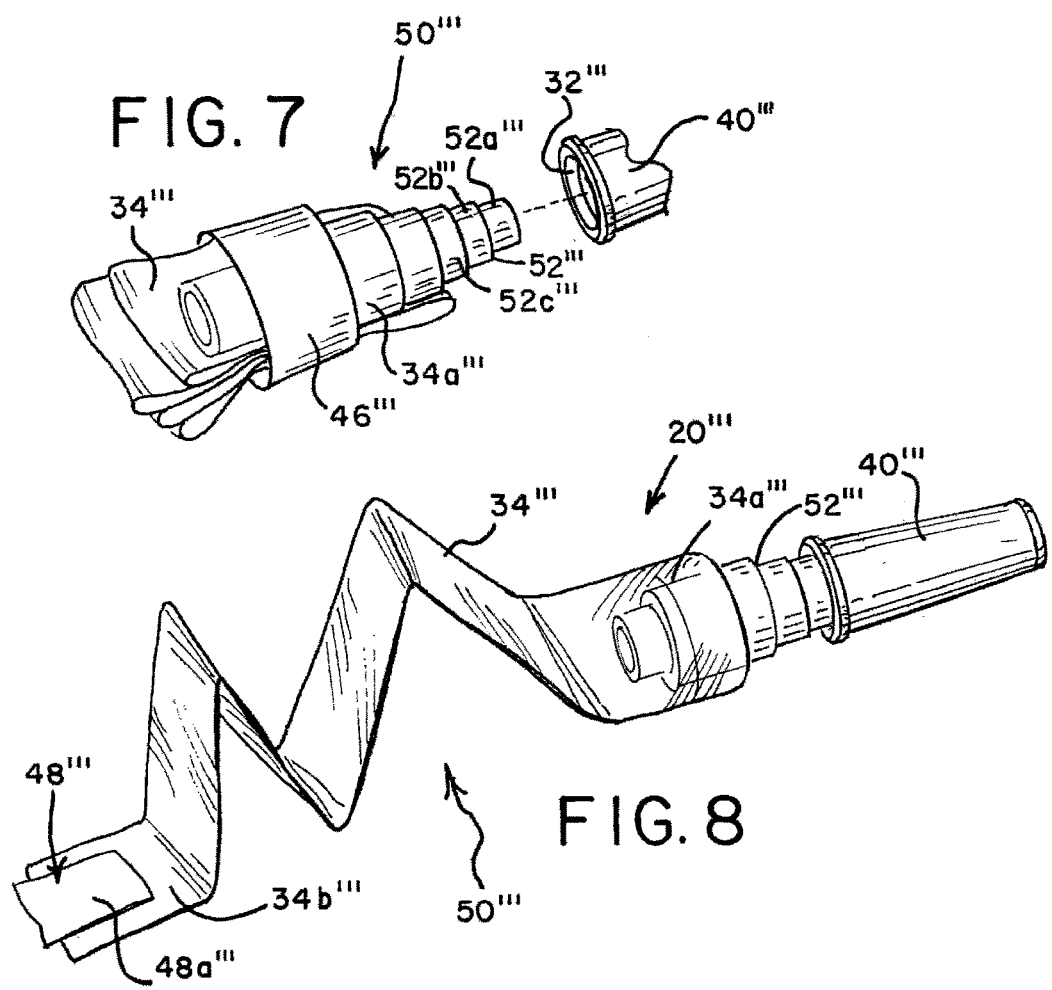

INTERMITTENT URINARY CATHETER ASSEMBLY AND AN ADAPTER ASSEMBLY FOR AN INTERMITTENT URINARY CATHETER

RELATED APPLICATION

This application is a U.S. National Stage of PCT International Patent Application No. PCT/US2013/031468, filed Mar. 14, 2013, which claims the benefit of and priority to U.S. Provisional Patent Application Ser. No. 61/716,176, filed Oct. 19, 2012, both of which are incorporated by reference herein.

FIELD OF THE DISCLOSURE

The present disclosure is generally related to intermittent catheters for use in draining urine from the human bladder and, more particularly, to intermittent urinary catheter assemblies for use by those facing catheter drainage issues such as wheelchair bound users and the like.

BACKGROUND OF THE DISCLOSURE

Intermittent catheterization is a good option for many users who suffer from various abnormalities of the urinary system. A common situation is where a single use, individually packaged, sterile catheter is used. An important criterion for any single use product is that it be user friendly since there will often not be trained medical personnel performing catheterization.

Due to the advancements that have been made in intermittent urinary catheter products, it is now quite common for users who require catheterization on a recurring basis to perform this procedure themselves. The intermittent urinary catheter products which are currently available render the catheterization procedure straightforward for many catheter users. However, this is not the case for some users such as those who are wheelchair bound who may encounter difficulty in being able to discharge urine from an intermittent urinary catheter directly into a toilet.

For wheelchair bound users who would otherwise be able to administer self-intermittent catheterization for voiding their bladder of urine multiple times per day, existing intermittent urinary catheter products have not provided a suitable solution for discharging urine from the catheter into a toilet, especially for allowing the users to remain in their wheelchair in close proximity to the toilet during the catheterization procedure without concern for urine spillage.

SUMMARY OF THE DISCLOSURE

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In the present disclosure, an intermittent urinary catheter assembly comprises a catheter tube having a proximal insertion end and a distal end remote from the proximal insertion end. The catheter tube has a lumen which extends from at or near the proximal insertion end to the distal end for draining urine from a human bladder. The catheter tube also has at least one drainage opening which extends through the catheter tube to the lumen at or near the proximal insertion end. The catheter tube further has a discharge opening which is associated with the distal end thereof to permit urine from a human bladder to be discharged. The urine is discharged through the discharge opening in the catheter tube after it has first passed from the human bladder, through the drainage opening, and through the lumen of the catheter tube.

The intermittent urinary catheter assembly includes a urine discharge sleeve associated with the discharge opening. The urine discharge sleeve has a compact stowed configuration and is extendable to a deployed configuration for directing urine to for example a receptacle, such as, a toilet at a location spaced from the catheter tube. In the compact stowed configuration, the urine discharge sleeve may be concertina or reverse folded or rolled. Optionally, the catheter tube has a protective sleeve covering at least a portion thereof for non-contaminated insertion while extending the proximal insertion end through a urethra until it is disposed within the bladder for urine drainage.

In one exemplary embodiment, a funnel is associated with the distal end of the catheter tube and defines the discharge opening wherein the urine discharge sleeve may have a first end secured to the funnel and a second, extendable end. Advantageously, the urine discharge sleeve may be concertina folded about the funnel, and a discharge funnel may be provided for extending the second end of the urine discharge sleeve. Alternatively, the urine discharge sleeve may be reverse folded and secured to the funnel utilizing a paper band, and a pull ring having an adhesive area may be secured to the second end of the urine discharge sleeve.

In another exemplary embodiment, a funnel is again associated with the distal end of the catheter tube and defines the discharge opening, but in this embodiment the urine discharge sleeve may have a first end secured to a fitting or nipple and a second, extendable end. The urine discharge sleeve may be concertina folded and disposed within a discharge funnel, or reverse folded and secured to the adapter by a paper band and, in the latter embodiment, a pull tab having an adhesive area thereon may suitably be secured to the second end of the urine discharge sleeve. Further, these embodiments may suitably comprise adapter assemblies where the fitting or nipple is adapted to be inserted into the funnel following which the second end of the urine discharge sleeve may be extended away from the funnel to a receptacle, e.g., a toilet.

Thus, the present disclosure is also directed to an adapter assembly for extending the point from which urine from a human bladder can be discharged from any conventional intermittent urinary catheter. The adapter assembly comprises a fitting or nipple having an axially extending urine passageway for insertion into the discharge opening at a urine discharge end of the intermittent urinary catheter. The adapter assembly may include a discharge funnel associated with, but separable from, the nipple, and a urine discharge sleeve within the discharge funnel which has a first end secured to the nipple and a second end secured to the discharge funnel. With this arrangement, the discharge funnel is separable from the nipple for extending the urine discharge sleeve so the discharge funnel can be positioned for urine discharge at a distance from the nipple.

BRIEF DESCRIPTION OF THE DRAWINGS

FIG. 1 is a perspective view of a first embodiment of intermittent urinary catheter assembly in accordance with the present disclosure;

FIG. 1A is a perspective view of the intermittent urinary catheter assembly of FIG. 1 with a concertina style urine discharge sleeve removed;

FIG. 2 is an enlarged perspective view of the drainage funnel being detached from the remainder of the assembly shown in FIGS. 1 and 1A;

FIG. 3 is a perspective view of a second embodiment of intermittent urinary catheter assembly in accordance with the present disclosure;

FIG. 4 is a perspective view of the intermittent urinary catheter assembly of FIG. 3 with a urine discharge sleeve being moved to an extended position;

FIG. 5 is a perspective view of the pull ring and urine discharge sleeve after the urine discharge sleeve has been substantially fully extended;

FIG. 6 is a front elevational view of an adapter assembly for use with an intermittent urinary catheter in accordance with the present disclosure;

FIG. 6A is a perspective view of the adapter assembly illustrated in FIG. 6 being inserted into an intermittent urinary catheter for use therewith;

FIG. 6B is a perspective view of the adapter assembly illustrated in FIG. 6 after insertion into the intermittent urinary catheter for use therewith;

FIG. 6C is a perspective view illustrating a drainage funnel and urine discharge sleeve of the adapter assembly of FIG. 6B being extended for use;

FIG. 6H is a perspective view of the adapter assembly of FIG. 6G illustrating the covering as it is being peeled away to expose the adhesive surface;

FIG. 6I is a perspective view of still another adapter assembly similar to FIG. 6D but provided with a clip style handle on the drainage funnel;

FIG. 6J is a perspective view illustrating a drainage funnel and urine discharge sleeve of the adapter assembly of FIG. 6I being extended for use;

FIG. 6K is an enlarged perspective view of the adapter assembly of FIG. 6I illustrating details of the clip style handle on the drainage funnel;

FIG. 6L is an enlarged perspective view of the clip style handle of FIG. 6K being used to secure the drainage funnel to a toilet during use;

FIG. 7 is a perspective view of another embodiment of adapter assembly as it is being inserted into an intermittent urinary catheter for use; and FIG. 8 is a perspective view illustrating a pull tab and urine discharge sleeve of the adapter assembly of FIG. 7 being extended for use.

DETAILED DESCRIPTION OF THE DISCLOSURE

Figure 6D:
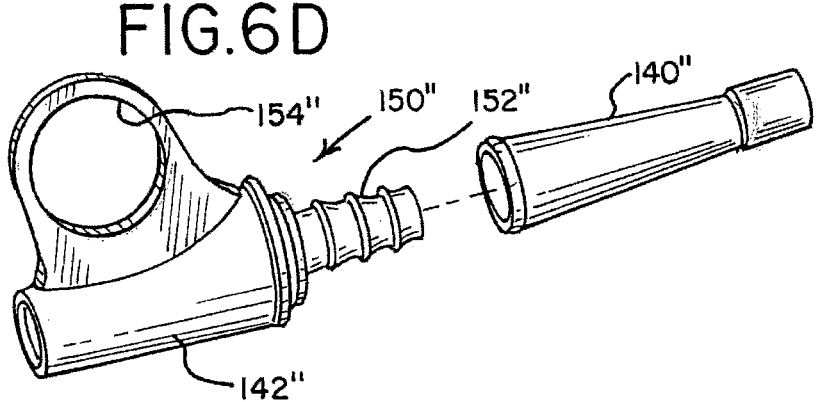
FIG. 6D is a perspective view of another embodiment of adapter assembly as it is being inserted into an intermittent urinary catheter for use.

In the illustrations given, and with reference first to FIGS. 1, 1A and 2, the reference numeral 20 designates generally an intermittent urinary catheter assembly in accordance with the present disclosure. The intermittent urinary catheter assembly 20 will be seen to comprise a catheter tube 22 having a proximal insertion end 24 and a distal end 26 which is located remote from the proximal insertion end 24. The catheter tube 22 has a conventional lumen 28 which extends from at or near the proximal insertion end 24 to the distal end 26 to accommodate the draining of urine from a human bladder. The catheter tube 22 also has at least one drainage opening 30 which extends through the catheter tube 22 to the lumen 28 in a location at or near the proximal insertion end 24. The catheter tube 22 further has a discharge opening 32 (FIG. 1A) associated with the distal end 26 of the catheter tube 22 to permit urine voided from a human bladder to be discharged therefrom. The urine is discharged through the discharge opening 32 in the catheter tube 22 after it passes from the human bladder, through the drainage opening 30, and through the lumen 28. In addition, the intermittent urinary catheter assembly 20 includes a urine discharge sleeve 34 associated with the discharge opening 32 and having a compact stowed configuration at or near the distal end 26 of catheter tube 22. In the embodiment shown in FIG. 1, urine discharge sleeve 34 has a compact stowed configuration at or near funnel 40. In the compact stowed configuration, the urine discharge sleeve may be compacted in any suitable manner. For example, urine discharge sleeve 34 may be folded, bunched, rolled, etc. The urine discharge sleeve 34 is extendable into a deployed configuration to direct urine flow and to, for example, reach a receptacle such as a toilet at a location spaced from the catheter tube 22 for directing urine to the toilet.

Still referring to FIGS. 1, 1A and 2, the intermittent urinary catheter assembly 20 optionally includes a protective sleeve 36 which covers at least a portion of the catheter tube 22 and extends from at or near the proximal insertion end 24 toward the distal end 26. While not shown, the protective sleeve 36 may be secured to an introducer tip, and it preferably extends to cover substantially the entire insertable portion of the catheter tube 22 to permit contamination-free gripping of the catheter tube 22 through the protective sleeve 36. The intermittent urinary catheter assembly 22 may include a funnel 40 associated with the distal end 26 of the catheter tube 22 to define the discharge opening 32 through which urine from a human bladder exits the catheter tube 22.

With the foregoing arrangement, the urine discharge sleeve 34 may include a first end 34a secured to the funnel 40 and a second, extendable end 34b, and in the stowed configuration, it may be concertina folded over the funnel 40 as shown in FIG. 1. In addition, a separate drainage funnel 42 may be provided for extending the second end 34b of the urine discharge sleeve 34 which may be secured to the drainage funnel 42 in any conventional manner. Preferably, the urine discharge sleeve 34 may be formed of polyethylene or a material having similar properties, and it may extend to a length of 300 mm or more to provide for convenient drainage for a wheelchair bound user.

With regard to the first end 34a of the urine discharge sleeve 34, it may be suitably secured to the funnel 40, which can be formed of rubber, in any conventional manner, e.g., by heat sealing or the like. Before the catheter tube 22 has been inserted into the urethra utilizing the protective sleeve 36, the drainage funnel 42 may be grasped with one hand to extend the urine discharge sleeve 34 as indicated by the arrow in FIG. 2.

Once the urine discharge sleeve 34 has been substantially fully extended, the drainage funnel 42 can be placed in or connected to any urine-receiving receptacle such as a toilet to permit urine voided from a human bladder to be discharged into the toilet after passing from the human bladder, through the drainage opening(s) 30, through the lumen 28 of the catheter tube 22, through the discharge opening 32 defined by the funnel 40, through the urine discharge sleeve 34, and through the drainage funnel 42 into the toilet or other urine-receiving receptacle.

Referring to FIGS. 3-5, the intermittent urinary catheter assembly 20' has certain similarities to the intermittent urinary catheter assembly 20 described above in connection with FIGS. 1, 1A and 2. Thus, the intermittent urinary catheter assembly 20' again comprises a catheter tube 22' having a proximal insertion end (not shown) and a distal end 26' which is located remote from the proximal insertion end. The catheter tube 22' again has a lumen (not shown) which extends from at or near the proximal insertion end to the distal end 26' to accommodate the draining of urine from a human bladder. The catheter tube 2T also again has at least one drainage opening (not shown) which extends through the catheter tube 2T to the lumen in a location which is at or near the proximal insertion end. The catheter tube 22' also again has a discharge opening 32' associated with the distal end 26' thereof and defined by a funnel 40' to permit urine voided from a human bladder to be discharged therefrom. In addition, the intermittent urinary catheter assembly 20' includes a urine discharge sleeve 34' associated with the funnel 40' defining the discharge opening 32' and having a compact stowed configuration. Urine discharge sleeve 34' is extendable into a deployed configuration to reach a receptacle such as a toilet.

In common with the embodiment illustrated in FIGS. 1, 1A and 2, the urine discharge sleeve 34' has a first end 34*a'* secured to the funnel 40' and a second, extendable end 34*b'*. However, unlike the embodiment illustrated in FIGS. 1, 1A and 2, the urine discharge sleeve 34' of the intermittent urinary catheter assembly 20' illustrated in FIGS. 3-5 is reverse folded in the compact stowed configuration and optionally secured to the funnel 40' by a retaining member, for example a band 46', such as a paper band. Alternatively, the urine discharge sleeve 34' may be rolled up in the compact stowed configuration. In addition, a pull ring 48' having an adhesive area 48*a'* (FIG. 5) is secured to the second end 34*b'* of the urine discharge sleeve 34'.

Referring specifically to FIG. 5, it will be seen that the pull ring 48' may be permanently secured to the second end 34*b'* of the urine discharge sleeve 34' as at 48*b'* and the adhesive area 48*a'* may comprise a releasable adhesive provided on the underside of the pull ring 48' to be exposed when the pull ring 48' is pulled away from the urine discharge sleeve 34', as shown.

Before the catheter tube 22' has been inserted into the urethra utilizing the protective sleeve 36' and the introducer tip (not shown), the pull ring 48' may be grasped through the opening 48*c'* utilizing a single finger on one hand to extend the urine discharge sleeve 34'.

Once the urine discharge sleeve 34' has been substantially fully extended into the deployed configuration by pulling as illustrated in FIG. 4, the pull ring 48 can be secured in any urine-receiving receptacle such as a toilet utilizing the adhesive area 48*a'* to permit urine voided from a human bladder to be discharged into the toilet after passing from the human bladder, through the drainage opening, through the lumen of the catheter tube 22', through the discharge opening 32' defined by the funnel 40', and through the urine discharge sleeve 34'.

Referring to FIGS. 6A-6C, the intermittent urinary catheter assembly 20" also has certain similarities to the intermittent urinary catheter assembly 20 described above in connection with FIGS. 1, 1A and 2. Thus, the intermittent urinary catheter assembly 20" again comprises a catheter tube 22" having a proximal insertion end (not shown) and a distal end 26" which is located remote from the proximal insertion end. The catheter tube 22" again has a lumen (not shown) which extends from at or near the proximal insertion end to the distal end 26" to accommodate the draining of urine from a human bladder. The catheter tube 22" also again has at least one drainage opening (not shown) which extends through the catheter tube 22" to the lumen in a location which is at or near the proximal insertion end. The catheter tube 22" also again has a discharge opening 32" associated with the distal end 26" thereof and defined by a funnel 40" to permit urine voided from a human bladder to be discharged therefrom. Also, the intermittent urinary catheter assembly 20" includes a urine discharge sleeve 34" associated with the funnel 40" defining the discharge opening 32" and having a compacted stowed configuration. Urine discharge sleeve 34" is extendable into a deployed configuration to reach a receptacle such as a toilet.

Unlike the embodiment illustrated in FIGS. 1, 1A and 2 described above, the urine discharge sleeve 34" comprises part of an adapter assembly 50" (FIG. 6) which includes a fitting 52" and a drainage funnel 42". In this embodiment, the urine discharge sleeve 34" has a first end 34*a"* secured to the fitting 52" (FIG. 6C) and a second, extendable end 34*b"* secured to the drainage funnel 42". The urine discharge sleeve 34" of the intermittent urinary catheter assembly 20" illustrated in FIGS. 6A-6C is concertina folded, in the compact stowed configuration, within the drainage funnel 42" portion of the adapter assembly 50" (FIG. 6) and is secured to both the drainage funnel 42" and the fitting 52" in any conventional manner. The adapter assembly 50" therefore comprises an assembly which includes the urine discharge sleeve 34", the drainage funnel 42", and the fitting 52" with the fitting 52" comprising a nipple having a urine passageway which is adapted for insertion into the funnel 40". The fitting or nipple 52" which is illustrated in FIGS. 6A-6C is commonly known as a Christmas tree fitting which can be safely secured within a structure such as the funnel 40" at the distal end 26" of the catheter tube 22".

Because the funnel 40" is typically formed of a rubber or rubber-like material, and as a result of the increasing diameter portions 52*a"*, 52*b"*, 52*c"*, etc. of the Christmas tree fitting 52", the user can very quickly and easily insert the Christmas tree fitting 52" into the funnel 40" until it is secured at which point the urine discharge sleeve 34" can be extended into the deployed configuration for use by pulling on the drainage funnel 52" which is initially disposed over the outer surface of the fitting or nipple 52" in frictional fit fashion but is easily separated therefrom (compare FIGS. 6B and 6C).

Figure 6E:
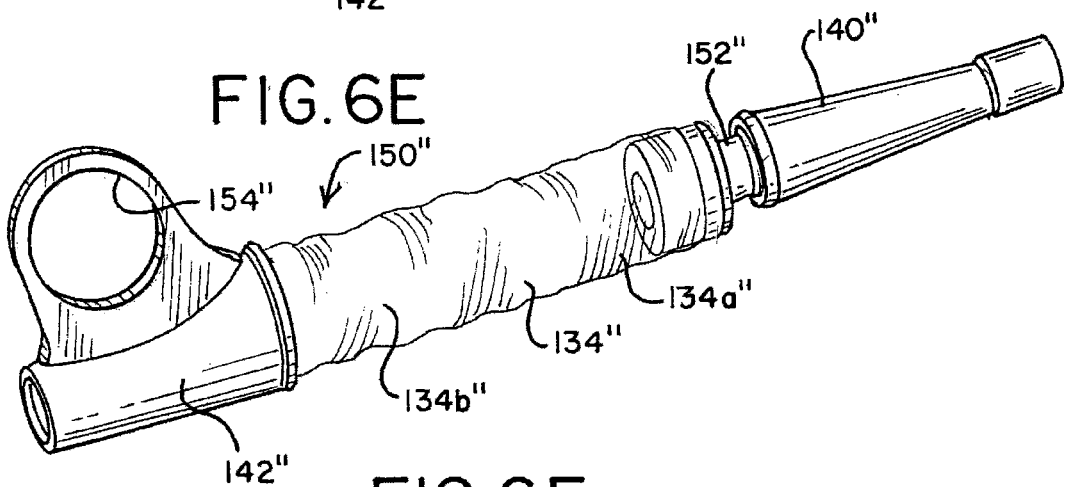
FIG. 6E is a perspective view illustrating a drainage funnel and urine discharge sleeve of the adapter assembly of FIG. 6D being extended for use.

Referring to FIGS. 6D-6E, an adapter assembly 150" is illustrated which is generally the same as the adapter assembly 50" illustrated in FIGS. 6 and 6A-6C with a single exception. As before, the adapter assembly 150" includes a fitting 152" and a drainage funnel 142". In this embodiment, the urine discharge sleeve 134" also has a first end 134*a"* secured to the fitting 152" (FIG. 6E) and a second, extendable end 134*b"* secured to the drainage funnel 142". As before, the urine discharge sleeve 134" of the intermittent urinary catheter assembly 120" illustrated in FIGS. 6D-6E is concertina folded, in the compact stowed configuration, within the drainage funnel 142" portion of the adapter assembly 150" and is secured to both the drainage funnel 142" and the fitting 152" in any conventional manner. The adapter assembly 150" therefore again comprises an assembly which includes the urine discharge sleeve 134", the drainage funnel 142", and the fitting 152" with the fitting 152" comprising a nipple having a urine passageway which is adapted for insertion into the funnel 140". As before, the fitting or nipple 152" which is illustrated in FIGS. 6D-6E can be safely secured within a structure such as the funnel 140" at the distal end 126" of the catheter tube 122".

As will be appreciated, the adapter assembly 150" differs from the adapter assembly 50" in that a large finger loop 154" is integrally formed on the outer surface of the drainage funnel 142" which makes the drainage funnel 142" easy to control even for those users with limited manual dexterity when separating it from the fitting or nipple 152" and extending the urine discharge sleeve 134" into the deployed configuration to reach a toilet as shown in FIG. 6E.

Figure 6F:
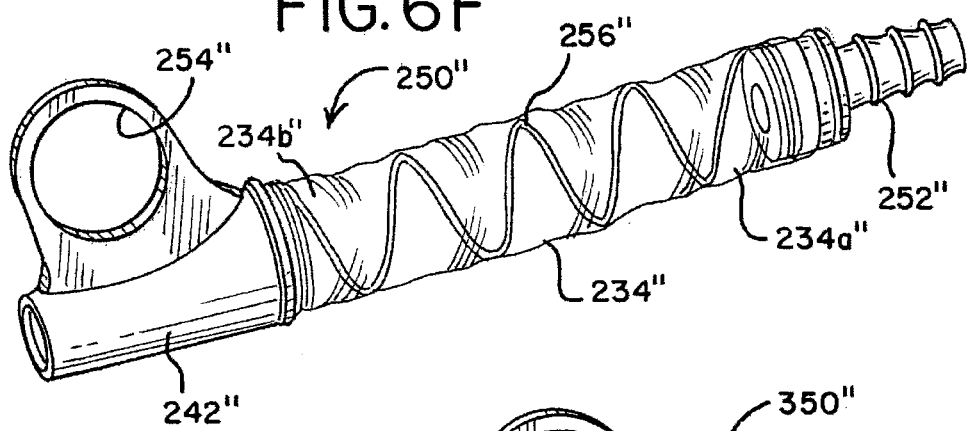
FIG. 6F is a perspective view of still another adapter assembly similar to FIG. 6E but provided with a urine discharge sleeve support structure.

Referring to FIG. 6F, an adapter assembly 250" is illustrated which is generally the same as the adapter assembly 150" illustrated in FIGS. 6D-6E with a single exception. As before, the adapter assembly 250" includes a fitting 252" and a drainage funnel 242". In this embodiment, the urine discharge sleeve 234" also has a first end 234a" secured to the fitting 252" and a second, extendable end 234b" secured to the drainage funnel 242". As before, the urine discharge sleeve 234" is concertina folded, in the compact stowed configuration, within the drainage funnel 242" portion of the adapter assembly 250" and is secured to both the drainage funnel 242" and the fitting 252" in any conventional manner. The adapter assembly 250" therefore again comprises an assembly which includes the urine discharge sleeve 234", the drainage funnel 242", and the fitting 252" with the fitting 252" comprising a nipple having a urine passageway which is adapted for insertion into the funnel 240". As before, the fitting or nipple 252" which is illustrated in FIG. 6F can be safely secured within a structure such as the funnel at the distal end of a catheter tube.

Also as before, the adapter assembly 250" has a large finger loop 254" integrally formed on the outer surface of the drainage funnel 242" which makes the drainage funnel 242" easy to control even for those users with limited manual dexterity when separating it from the fitting or nipple 252" and extending the urine discharge sleeve 234" to a toilet as shown in FIG. 6F.

However, unlike the embodiment illustrated in FIGS. 6D-6E, the urine discharge sleeve 234" includes a plastic support structure 256" similar to a coiled spring molded into the concertina folded sleeve but which is collapsible to be disposed within the drainage funnel 242" until the drainage funnel is separated from the fitting or nipple 252".

Figure 6G:
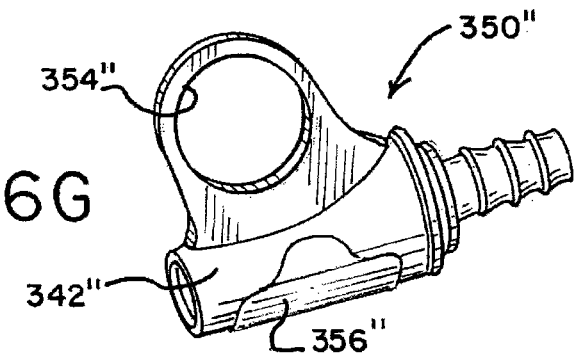
FIG. 6G is a perspective view of the adapter assembly of FIG. 6D provided with a covered adhesive surface to secure the drainage funnel to a toilet.

Referring to FIGS. 6G-6H, an adapter assembly 350" is illustrated which is generally the same as the adapter assemblies 150" and 250" illustrated in FIGS. 6D-6F with a single exception. In this case, a covered adhesive area 348a" (FIG. 6H) is provided on the outer surface of the drainage funnel 342" on the side opposite the large finger loop 354" for adhesively securing the drainage funnel 342" to a receptacle such as a toilet after a protective covering 356" is peeled away (FIG. 6H).

Referring next to FIGS. 6I-6L, an adapter assembly 450" is illustrated which is also generally the same as the adapter assemblies 150" and 250" illustrated in FIGS. 6D-6F with a single exception relating to the structure for handling the drainage funnel. In this case, instead of a large finger loop such as 154" in FIGS. 6D-6F being integrally formed on the outer surface of the drainage funnel 442", a clip style handle 456" is provided for extending the drainage funnel and also for securing the drainage funnel to a toilet 458" during use. As shown, a user can insert several fingers into the clip style handle 456" to extend the urine drainage sleeve 434" into the deployed configuration (FIG. 6J) and the clip style handle 456" can then be spread open to clip the drainage funnel 442" to the toilet 458" as shown in FIG. 6L.

Referring to FIGS. 7 and 8, the intermittent urinary catheter assembly 20''' also has certain similarities to the intermittent urinary catheter assembly 20 described above in connection with FIGS. 1, 1A and 2. Thus, the intermittent urinary catheter assembly 20''' again comprises a catheter tube having a proximal insertion end and a distal end which is located remote from the proximal insertion end. The catheter tube again has a lumen which extends from at or near the proximal insertion end to the distal end to accommodate the draining of urine from a human bladder. The catheter tube also again has at least one drainage opening which extends through the catheter tube to the lumen in a location which is at or near the proximal insertion end. The catheter tube also again has a discharge opening 32' associated with the distal end thereof and defined by a funnel 40' to permit urine voided from a human bladder to be discharged therefrom. Also, the intermittent urinary catheter assembly 20''' includes a urine discharge sleeve 34''' associated with the funnel 40''' defining the discharge opening 32''' and extendable to a receptacle such as a toilet.

Like the embodiments illustrated in FIGS. 6 and 6A-6L, and unlike the embodiment illustrated in FIGS. 1, 1A and 2, the urine discharge sleeve 34''' comprises part of an adapter assembly 50' which includes a fitting 52'''. In this embodiment, the urine discharge sleeve 34' has a first end 34a''' secured to the fitting 52''' and a second, extendable end 34b'''. The urine discharge sleeve 34" of the intermittent urinary catheter assembly 20''' illustrated in FIGS. 7 and 8 is reverse folded in the compact stowed configuration and secured to the fitting 52''' by a retaining member 46", for example a band, such as a paper band, and this adapter assembly 50' is comprised of the urine discharge sleeve 34', the fitting 52''' and the band 46" with the fitting 52''' comprising a nipple having a urine passageway which is adapted for insertion into the funnel 40'. The fitting or nipple 52''' illustrated in FIGS. 7 and 8 can be safely secured within a structure such as the funnel 40'''.

Because the funnel 40''' is typically formed of a rubber or rubber-like material, and as a result of the increasing diameter portions 52a''', 52b''', 52c''', etc. of the fitting 52''', the user can very quickly and easily insert the fitting 52''' into the funnel 40''' until it is secured at which point the urine discharge sleeve 34''' can be extended for use.

In this connection, a pull tab 48''' having an adhesive area 48a''' is secured to the second end 34b''' of the urine discharge sleeve 34''' to be used in extending the discharge sleeve 34''' into the deployed configuration and adhesively securing the second end 34b''' to a receptacle such as a toilet.

With regard to the two embodiments illustrated in FIGS. 3-5 and 7-8, respectively, it will be appreciated that when the user pulls on the pull ring 48' or the pull tab 48', it releases the folded urine discharge sleeves 34' and 34' from the paper bands 46' and 46', respectively.

As will be appreciated, the embodiments illustrated in all of FIGS. 6, 6A-6L, 7 and 8 give
users of conventional intermittent urinary catheters the option of being able to extend the point from which urine is discharged from a conventional intermittent urinary catheter by purchasing an adapter assembly which quickly and easily connects to the funnel of the catheter and is quickly and easily extendable by pulling on the extendable end of a urine discharge sleeve.

Advantageously, all of the urine discharge sleeves can be extended to their full length suitably ranging from about 300 mm to about 430 mm to allow the user to administer self intermittent catheterization while remaining seated in a wheelchair during the procedure. Because of the length of the urine discharge sleeves, urine voided from a human bladder through an intermittent urinary catheter can be directed into a receptacle such as a toilet by causing the urine exiting the catheter to pass through the urine discharge sleeves.

While the foregoing sets forth details of the present disclosure, it will be appreciated by those skilled in the art that the details herein given may be varied without departing from the true spirit and scope of the appended claims.

What is claimed is:

1. An intermittent urinary catheter assembly, comprising:
a catheter including a catheter tube having a proximal insertion end and a distal end remote from the proximal insertion end, the catheter tube having a lumen extending from at or near the proximal insertion end to the distal end for draining urine from a human bladder, and at least one drainage opening extending through the catheter tube to the lumen at or near the proximal insertion end;
a discharge opening associated with a distal end portion of the catheter to permit urine from a human bladder to be discharged from the catheter after first passing through the drainage opening into and through the lumen of the catheter tube; and
a urine discharge sleeve having a proximal end portion and a distal end portion, the proximal end portion of the urine discharge sleeve being secured to the distal end portion of the catheter, and the urine discharge sleeve having an initial, pre-use compact stowed configuration wherein the urine discharge sleeve is reverse folded over the distal end portion of the catheter, the urine discharge sleeve being extendable into a deployed configuration wherein the distal end portion of the urine discharge sleeve is extended away from the distal end portion of the catheter for directing urine flow discharged from the discharge opening.

2. The intermittent urinary catheter of claim 1 wherein the distal end portion of the catheter defines a discharge funnel that defines the discharge opening, wherein the proximal end portion of the urine discharge sleeve is secured to the discharge funnel.

3. The intermittent urinary catheter of claim 1 further including a pull ring associated with the urine discharge sleeve for extending the urine discharge sleeve into the deployed configuration.

4. The intermittent urinary catheter assembly of claim 3 including an adhesive area on a portion of the pull ring and a peelable protective covering over the adhesive area for removal to expose the adhesive for securing to a receptacle.

5. The intermittent urinary catheter of claim 1 wherein the urine discharge sleeve includes an adhesive area associated therewith for attaching the urine discharge sleeve to a receptacle.

6. The intermittent urinary catheter assembly of claim 1 wherein the urine discharge sleeve is secured in the compact stowed configuration by a retaining member.

7. The intermittent urinary catheter assembly of claim 1 wherein the urine discharge sleeve is secured in the stowed configuration by a band.

8. The intermittent urinary catheter assembly of claim 1 including a collapsible support structure associated with the urine discharge sleeve.

9. The intermittent urinary catheter assembly of claim 1 wherein the urine discharge sleeve is extendable to a length of between about 300 mm and 430 mm.

10. The intermittent urinary catheter assembly of claim 1 further including a protective sleeve covering at least a portion of the catheter tube to accommodate non-contaminated insertion of the catheter tube into and through a urethra.

11. An intermittent urinary catheter assembly, comprising:
a catheter including a catheter tube having a proximal insertion end and a distal end remote from the proximal insertion end, the catheter tube having a lumen extending from at or near the proximal insertion end to the distal end for draining urine from a human bladder, and at least one drainage opening extending through the catheter tube to the lumen at or near the proximal insertion end;
a discharge opening associated with the distal end portion of the catheter to permit urine from a human bladder to be discharged from the catheter after first passing through the drainage opening into and through the lumen of the catheter tube;
a protective sleeve covering at least a portion of the catheter tube; and
a separate urine discharge sleeve having a proximal end portion and a distal end portion, the proximal end portion of the urine discharge sleeve being attached to the distal end portion of the catheter, the urine discharge sleeve having an initial, pre-use compact stowed configuration wherein the urine discharge sleeve is reverse folded over the distal end portion of the catheter, the urine discharge sleeve having a deployed configuration wherein distal end portion of the urinary discharge sleeve is extended away from the discharge opening to a receptacle such that the urine discharge sleeve in the deployed configuration directs urine draining from the discharge opening associated with the catheter tube to the receptacle.

12. The intermittent urinary catheter of claim 11 wherein the distal end portion of the catheter defines a discharge funnel that defines the discharge opening, wherein the proximal end portion of the urine discharge sleeve is secured to the discharge funnel.

13. The intermittent urinary catheter of claim 11 further including a pull ring associated with the urine discharge sleeve for extending the urine.

14. The intermittent urinary catheter assembly of claim 13 including an adhesive area on a portion of the pull ring and a peelable protective covering over the adhesive area for removal to expose the adhesive for securing to a receptacle.

15. The intermittent urinary catheter assembly of claim 11 wherein the urine discharge sleeve includes an adhesive area associated therewith for attaching the urine discharge sleeve to a receptacle.

16. The intermittent urinary catheter assembly of claim 11 wherein the urine discharge sleeve is secured in the compact stowed configuration by a retaining member.

17. The intermittent urinary catheter assembly of claim 11 wherein the urine discharge sleeve is secured in the stowed configuration by a band.

18. The intermittent urinary catheter assembly of claim 11 including a collapsible support structure associated with the urine discharge sleeve.

19. The intermittent urinary catheter assembly of claim 11 wherein the urine discharge sleeve is extendable to a length of between about 300 mm and 430 mm.

* * * * *